United States Patent
Xie

(10) Patent No.: US 11,154,541 B2
(45) Date of Patent: Oct. 26, 2021

(54) METHODS FOR TREATING AORTIC VALVE STENOSIS WITH A HEDGEHOG PATHWAY INHIBITOR

(71) Applicant: The Trustees of Indiana University, Indianapolis, IN (US)

(72) Inventor: Jingwu Xie, Carmel, IN (US)

(73) Assignee: The Trustees of Indiana University, Indianapolis, IN (US)

( * ) Notice: Subject to any disclaimer, the term of this patent is extended or adjusted under 35 U.S.C. 154(b) by 0 days.

(21) Appl. No.: 16/457,552

(22) Filed: Jun. 28, 2019

(65) Prior Publication Data
US 2020/0000784 A1    Jan. 2, 2020

Related U.S. Application Data

(60) Provisional application No. 62/692,288, filed on Jun. 29, 2018.

(51) Int. Cl.
| | | |
|---|---|---|
| *A61P 9/10* | (2006.01) | |
| *A61K 31/4402* | (2006.01) | |
| *A61K 31/5377* | (2006.01) | |
| *A61K 31/517* | (2006.01) | |
| *A61K 31/437* | (2006.01) | |
| *A61K 31/454* | (2006.01) | |
| *A61K 31/502* | (2006.01) | |
| *A61K 31/59* | (2006.01) | |
| *A61K 33/36* | (2006.01) | |
| *A61K 31/496* | (2006.01) | |
| *A61K 31/166* | (2006.01) | |
| *A61K 31/444* | (2006.01) | |
| *A61K 31/505* | (2006.01) | |
| *A61K 31/4365* | (2006.01) | |
| *A61K 31/395* | (2006.01) | |
| *A61K 39/395* | (2006.01) | |
| *A61B 8/08* | (2006.01) | |
| *A61B 5/318* | (2021.01) | |
| *A61B 5/329* | (2021.01) | |
| *A61K 31/58* | (2006.01) | |
| *C07K 16/18* | (2006.01) | |
| *A61P 1/16* | (2006.01) | |

(52) U.S. Cl.
CPC .......... *A61K 31/4402* (2013.01); *A61B 5/318* (2021.01); *A61B 5/329* (2021.01); *A61B 8/0883* (2013.01); *A61K 31/166* (2013.01); *A61K 31/395* (2013.01); *A61K 31/437* (2013.01); *A61K 31/4365* (2013.01); *A61K 31/444* (2013.01); *A61K 31/454* (2013.01); *A61K 31/496* (2013.01); *A61K 31/502* (2013.01); *A61K 31/505* (2013.01); *A61K 31/517* (2013.01); *A61K 31/5377* (2013.01); *A61K 31/58* (2013.01); *A61K 33/36* (2013.01); *A61K 39/3955* (2013.01); *A61P 9/10* (2018.01); *A61P 1/16* (2018.01); *C07K 16/18* (2013.01)

(58) Field of Classification Search
CPC ... A61P 9/10; A61K 39/3955; A61K 31/4402; A61K 31/5377; A61K 31/517; A61K 31/437; A61K 31/454; A61K 31/4365; A61K 31/502; A61K 33/36; A61K 31/59; A61K 31/166; A61K 31/444; A61K 31/505; A61K 31/496; A61K 31/395
See application file for complete search history.

(56) References Cited

U.S. PATENT DOCUMENTS

2016/0341726 A1 * 11/2016 Humphreys ......... C12N 5/0668

OTHER PUBLICATIONS

Boudoulas et al, 2013. Cardiology. 126:139-152.*
Hirsova et al, 2013. PLOS One. 8(7): e70599.*
Faggiano P, Antonini-Canteen F, Baldessin F, Lorusso R, D'Aloia A, Cas LD. Epidemiology and cardiovascular risk factors of aortic stenosis. Cardiovasc Ultrasound. 2006;4:27.
Bonow RO, Greenland P. Population-wide trends in aortic stenosis incidence and outcomes. Circulation. 2015;131(11):969-971.
Coffey S, Cox B, Williams MJ. The prevalence, incidence, progression, and risks of aortic valve sclerosis: a systematic review and meta-analysis. J Am Coll Cardiol. 2014;63(25 Pt A):2852-2861.
Edeling M, Ragi G, Huang S, Pavenstadt H, Susztak K. Developmental signalling pathways in renal fibrosis: the roles of Notch, Wnt and Hedgehog. Nat Rev Nephrol. 201612(7):426-439.
Xie J, Murone M, Luoh SM, et al. Activating Smoothened mutations in sporadic basal-cell carcinoma. Nature. 1998;391(6662):90-92.
Mao J, Ligon KL, Rakhlin EY, et al. A novel somatic mouse model to survey tumorigenic potential applied to the Hedgehog pathway. Cancer Res. 2006;66(20):10171-10178.
Lam CW, Xie J, To KF, et al. A frequent activated smoothened mutation in sporadic basal cell carcinomas. Oncogene. 1999;18(3):833-836.
Ethowmick NA, Chytil A, Plieth D, et al. TGF-beta signaling in fibroblasts modulates the oncogenic potential of adjacent epithelia. Science. 2004;303(5659):848-851.
Damen FW, Berman AG, Soepriatna AH, et al. High-Frequency 4-Dimensional Ultrasound (4DUS): A Reliable Method for Assessing Murine Cardiac Function. Tomography. 2017;3(4)180-187.
Casaclang-Verzosa G, Enriquez-Sarano M, Villaraga HR, Miller JD. Echocardiographic Approaches and Protocols for Comprehensive Phenotypic Characterization of Valvular Heart Disease in Mice. J Vis Exp. 2017(120).

(Continued)

*Primary Examiner* — Zachary C Howard
(74) *Attorney, Agent, or Firm* — Faegre Drinker Biddle & Reath LLP

(57) ABSTRACT

Methods of treating a valvular heart disease are provided. Methods for treating valvular heard disease include administering to a subject a therapeutically effective amount of at least one hedgehog pathway inhibitor. Also provided are methods for reducing fibrosis in a subject, which comprise administering to the subject a therapeutically effective amount of at least one hedgehog pathway inhibitor.

10 Claims, 8 Drawing Sheets

(56) References Cited

OTHER PUBLICATIONS

Chu Y, Lund DD, Doshi H, et al. Fibrotic Aortic Valve Stenosis in Hypercholesterolemic/Hypertensive Mice. Arterioscler Thromb Vasc Biol. 2016;36(3):466-474.

Sekulic A, Migden MR, Oro AE, et al. Efficacy and safety of vismodegib in advanced basal-cell carcinoma. N Engl J Med. 2012;366(23):2171-2179.

Sekulic A, Migden MR, Basset-Seguin N, et al. Long-term safety and efficacy of vismodegib in patients with advanced basal cell carcinoma: final update of the pivotal ERIVANCE BCC study. BMC Cancer 2017;17(1):332.

Jacobsen AA, Aldahan AS, Hughes OB, Shah VV, Strasswimmer J. Hedgehog Pathway Inhibitor Therapy for Locally Advanced and Metastatic Basal Cell Carcinoma: A Systematic Review and Pooled Analysis of Interventional Studies. JAMA Dermatol. 2016;152(7):816-824.

Dummer R, Guminski A, Gutzmer R, et al. The 12-month analysis from Basal Cell Carcinoma Outcomes with LDE225 Treatment (BOLT): A phase II, randomized, double-blind study of sonidegib in patients with advanced basal cell carcinoma. J Am Acad Dermatol. 2016;75(1):113-125 e115.

\* cited by examiner

S100A4cre-SmoM2+        S100A4cre+SmoM2+

S100A4cre-SmoM2+        S100A4cre+SmoM2+

S100A4cre-SmoM2+

S100A4cre+SmoM2+

METHODS FOR TREATING AORTIC VALVE STENOSIS WITH A HEDGEHOG PATHWAY INHIBITOR

CROSS-REFERENCE TO RELATED APPLICATIONS

This application claims the benefit of U.S. provisional patent application No. 62/692,288, filed on Jun. 29, 2018, which is hereby incorporate by reference in its entirety.

FIELD

Various aspects and embodiments disclosed herein relate generally to the treatment of diseases characterized by the formation of valuvular heart diseases (VHDs).

BACKGROUND

Valvular heart diseases (VHDs) are a serious but under-appreciated public health problem, with over 5 million Americans diagnosed with VHDs each year. The prevalence of aortic valve stenosis (AS), a major subtype of VHD and detected by echocardiography, increases with age, with >10% of the elderly (>75 years) having a VHD. VHD eventually progresses to cause severe aortic stenosis with obstruction to left ventricular (LV) outflow, and many patients require aortic valve replacement (AVR). With the growing aging population, a high prevalence and a high medical burden due to aortic valve stenosis is anticipated in coming years. To date, there are no effective treatments for VHDs. Development of new treatment regimens that would reduce the effect of VHDs on a patient is much needed.

SUMMARY

According to one example, ("Example 1"), a method of treating a valvular heart disease in a subject comprises administering to the subject a therapeutically effective amount of at least one hedgehog pathway inhibitor.

According to one example ("Example 2"), a method of reducing fibrosis in a subject comprises administering to the subject a therapeutically effective amount of at least one hedgehog pathway inhibitor.

According to another example ("Example 3"), further to Example 1 or Example 2, the at least one hedgehog pathway inhibitor comprises: at least one smoothened (SMO) antagonist; at least one antagonist of GLI1, GLI2, and/or GLI3; at least one agonist of PTCH1 and/or PTCH2; or any combination thereof.

According to another example ("Example 4"), further to any of Examples 1-3, the at least one hedgehog pathway inhibitor comprises at least one of: vismodegib, sonidegib, BMS-833923, TAK-441, glasdegib, taladegib, saridegib, arsenic trioxide, PF-5274857, MRT-92, GANT-58, GANT-61, RU-SKI 43, sonic hedgehog (Shh) monoclonal antibody 5E1, itraconazole, and robotnikinin.

According to another example ("Example 5"), further to any of Examples 1-4, the method further includes the step of: identifying a subject at risk of having a valvular heart disease and/or identifying a subject having a valvular heart disease or a symptom related to the valvular heart disease.

According to another example ("Example 6"), further to any of Examples 1-5, the valvular heart disease comprises at least one disease process involving one or more of the four valves of the heart.

According to another example ("Example 7"), further to any of Examples 1-6, the valvular heart disease comprises at least one disease selected from: aortic valve stenosis, mitral valve stenosis, tricuspid valve stenosis, pulmonary valve stenosis, aortic valve regurgitation, mitral valve regurgitation, tricuspid valve regurgitation, pulmonary valve regurgitation, aortic valve calcification, mitral valve calcification, tricuspid valve calcification, pulmonary valve calcification, heart murmur associated with dysfunctional valves.

According to another example ("Example 8"), further to any of Examples 1-7, the therapeutically effective amount of the at least one hedgehog pathway inhibitor is administered daily to the subject in a single dose.

According to another example ("Example 9"), further to any of Examples 1-8, the therapeutically effective amount of the at least one hedgehog pathway inhibitor is administered daily to the subject in multiple doses.

According to another example ("Example 10"), further to any of Examples 1-9, a dose of the at least one hedgehog pathway inhibitor is from about 15 mg to about 1000 mg, from about 50 mg to about 500 mg, from about 50 mg to about 400 mg, from about 50 mg to about 300 mg, from about 50 mg to about 250 mg, from about 100 mg to about 200 mg, about 50 mg, about 100 mg, about 150 mg, about 200 mg, or about 250 mg of the hedgehog pathway inhibitor.

According to another example ("Example 11"), further to any of Examples 1-10, the at least one hedgehog pathway inhibitor is vismodegib and/or sonidegib.

According to another example ("Example 12"), further to any of Examples 1-11, the subject comprises a human or an animal.

According to another example ("Example 13"), further to any of Examples 1-12 the subject is diagnosed with a valvular heart disease and/or a related symptom.

According to another example ("Example 14"), further to any of Examples 1-13, the method further includes identifying a subject at risk of developing fibrosis and/or identifying a subject having fibrosis or a symptom related to fibrosis.

According to another example ("Example 15"), further to Example 14, the fibrosis comprises atrial fibrosis, endomyocardial fibrosis, and/or arterial stiffness.

BRIEF DESCRIPTION OF THE DRAWINGS

The patent or application file contains at least one drawing executed in color. Copies of this patent or patent application publication with color drawings will be provided by the Office upon request and payment of the necessary fee.

DESCRIPTION

Figure 1:
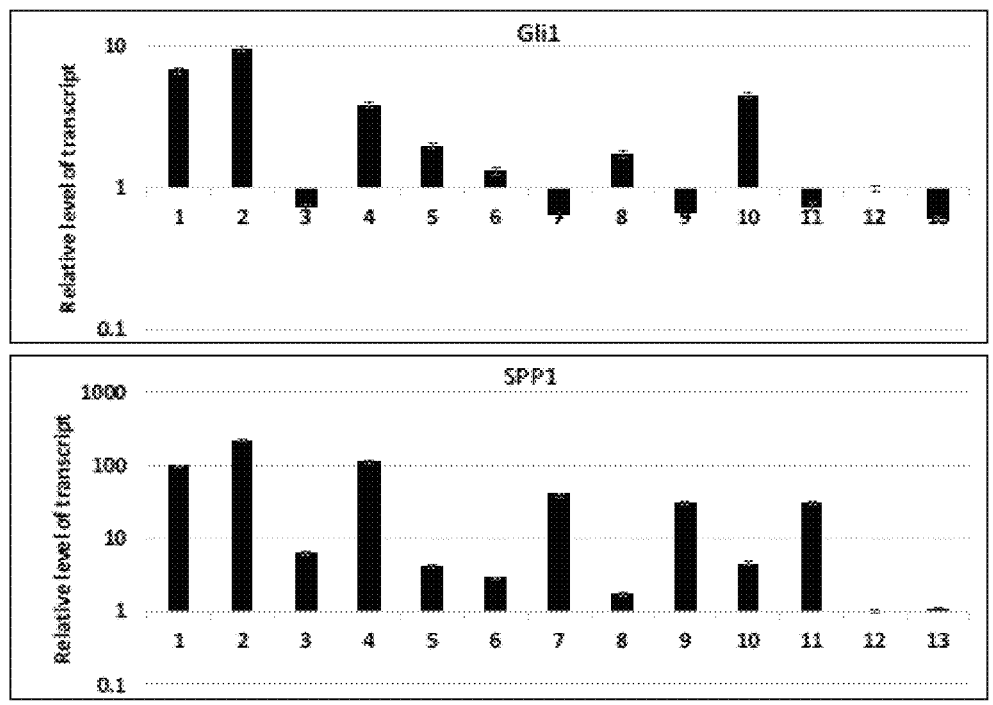
FIG. 1: Bar graphs summarizing results of real-time PCR analysis of either GLI1 (top panel) or SPP1 (bottom panel) gene expression in human aortic valves with or without fibrosis.

For the purposes of promoting an understanding of the principles of the novel technology, reference will now be made to various embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Unless explicitly stated otherwise or clearly implied otherwise, as used herein, the term "about" refers to a range of values that are within 10 percent (plus or minus) of a stated value; e.g. about 1.0 encompasses values of 0.90 to 1.10. Unless otherwise clear from context, all numerical values provided herein are modified by the term 'about'.

The term "treating" as used herein, unless explicitly stated or implied otherwise, includes administering to a human or an animal patient at least one dose of a compound. Treating includes lessening the likelihood and/or severity of at least one disease as well as limiting the length/duration of an illness, or the severity of an illness. Treating a patient may or may not result in a cure of the disease or condition. The term "treating" refers to partially or completely alleviating, ameliorating, delaying onset of, improving, inhibiting progression of, relieving, and/or reducing incidence of one or more symptoms or causes of a particular disease, disorder or condition. Treatment may be administered to a subject who does not exhibit signs of a disease, disorder, and/or condition, and/or to a subject who exhibits only early signs of a disease, disorder, and/or condition for the purpose of decreasing the risk of developing pathology associated with the disease, disorder, and/or condition.

As used herein, unless explicitly stated otherwise or clearly implied otherwise the terms "therapeutically effective dose," "therapeutically effective amounts," and the like, refer to any amount of a compound that has a net positive effect on health and well being of a human or other animal. Therapeutic effects may include an improvement in longevity, quality of life and the like, and may also include a reduced susceptibility to developing a disease, disorder, and/or condition, or slow or prevent deteriorating health or well being. The effects may be immediately realized after a single dose and/or treatment or they may be cumulatively realized after a series of doses and/or treatments. A "therapeutically effective amount" in general means any amount that, when administered to a subject or animal for treating a disease, is sufficient to effect the desired degree of treatment for the disease, disorder, and/or condition at a reasonable benefit/risk ratio applicable to medical treatment. It can be understood, however, that the total daily usage of the compounds of the disclosure can be decided by the attending physician within the scope of sound medical judgment. The specific therapeutically effective dose level for any particular patient can depend upon a variety of factors including the disorder being treated and the severity of the disorder; activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts.

Actual dosage levels of compounds in the pharmaceutical compositions of this disclosure can be varied so as to obtain an amount of the compound(s) that is effective to achieve the desired therapeutic response for a particular patient, compositions and mode of administration.

As used herein, "inhibition" or "inhibitory activity" each encompass whole or partial reduction of activity or effect of an enzyme, receptor, transcription factor, or other biologically active polypeptide, or all and/or part of a pathway that includes the biologically active polypeptide. The biologically active polypeptide may be affected either directly or indirectly by the inhibitor, and/or a pathway may be affected either directly or indirectly by the activity of the polypeptide, which itself is affected either directly or indirectly by the inhibitor.

As used herein, the term "pharmaceutically acceptable salt" is defined as a salt wherein the desired biological activity of the inhibitor is maintained and which exhibits a minimum of undesired toxicological effects. Pharmaceutically acceptable salts are derivatives of the disclosed compounds wherein the parent compound is modified by converting an existing acid or base moiety to its salt form. Non-limiting examples of such salts include: (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

Pharmaceutically acceptable salts include salts of compounds described herein that are safe and effective for use in mammals and that possess a desired therapeutic activity. Pharmaceutically acceptable salts include salts of acidic or basic groups present in compounds described herein. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds described herein may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used in accordance with the present disclosure, see, e.g., Berge, et al., 66 J. PHARM. SCI. 1-19 (1977); Haynes, et al., J. Pharma. Sci., Vol. 94, No. 10, October 2005, pgs. 2111-2120; P. Stahl, et al., HANDBOOK OF PHARMACEUTICAL SALTS: PROPERTIES, SELECTION AND USE, (VCHA/Wiley-VCH, 2002).

The compounds described herein and their pharmaceutically acceptable salts may be formulated as pharmaceutical compositions for administration in accordance with the present methods. Acceptable pharmaceutical formulations and processes for making the same are known in the art for both humans and non-human mammals. See, e.g., REMINGTON: THE SIENCE AND PRACTICE OF PHARMACY (A. Gennaro, et al., eds., $19^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound described herein or a pharmaceutically acceptable salt thereof.

Pharmaceutical formulations of compounds described herein may be suitable for oral, parenteral (including subcutaneous, intradermal, intramuscular and intravenous) and/or rectal administration. The formulations may be presented in unit dosage form and may be prepared by any of the methods well known in the art of pharmacy. All methods include the step of bringing into association the active ingredient (i.e., the compound or pharmaceutically acceptable salt of the present disclosure) with the carrier. In general, the formulations are prepared by uniformly and intimately bringing into association the active ingredient with a liquid carrier or, a finely divided solid carrier or both, and then, if necessary, forming the associated mixture into the desired dosage form.

The pharmaceutical formulations of the present disclosure suitable for oral administration may be presented as discrete units, such as a capsule, cachet, tablet, or lozenge, each containing a predetermined amount of the active ingredient. The active ingredient may be present as a powder or granules; as a solution or a suspension in an aqueous liquid or non-aqueous liquid such as a syrup, elixir or a draught; or as an oil-in-water liquid emulsion or a water-in-oil liquid emulsion. The formulation may also be presented as a bolus, electuary or paste.

The pharmaceutical formulations of the present disclosure suitable for parenteral administration include aqueous and non-aqueous sterile injection solutions, and may also include an antioxidant; a buffer; a bacteriostat; a solution which renders the composition isotonic with the blood of the recipient; and aqueous and non-aqueous sterile suspensions which may contain, for example, a suspending agent and a thickening agent. The formulations may be presented in a single dose unit or multi-dose containers, and may be stored in a lyophilized condition requiring the addition of a sterile liquid carrier prior to use.

The term "pharmaceutically acceptable carrier", unless explicitly stated or clearly implied otherwise, is used herein to describe any ingredient other than the active compound(s) that maybe included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

As used herein, "hedgehog pathway inhibitors" or "hedgehog inhibitors" include, but are not limited to, vismodegib, sonidegib, BMS-833923, TAK-441, glasdegib, taladegib, saridegib, arsenic trioxide, PF-5274857, MRT-92, GANT-58, GANT-61, RU-SKI 43, sonic hedgehog (Shh) monoclonal antibody 5E1, itraconazole, and robotnikinin.

As used herein, "valvular heart diseases" or "VHDs" include, but are not limited to: any disease processes involving one or more of the four valves of the heart; stenosis including aortic valve stenosis, mitral valve stenosis, tricuspid valve stenosis, and pulmonary valve stenosis; regurgitation including aortic valve regurgitation, mitral valve regurgitation, tricuspid valve regurgitation, and pulmonary valve regurgitation; calcification; and heart murmur associated with dysfunctional valves.

As used herein, "fibrosis" refers to the formation of excess fibrous connective tissue in an organ or tissue in a reparative or reactive process. Fibrosis is similar to the process called scarring, in that both involve stimulated fibroblasts laying down connective tissue, including collagen and glycosaminoglycans. The fibrosis can be initiated when immune cells such as macrophages release soluble factors that stimulate fibroblasts. The most well characterized pro-fibrotic mediator can be TGF beta, which is released by macrophages as well as any damaged tissue between surfaces called interstitium. Other soluble mediators of fibrosis include, but are not limited to, CTGF, platelet-derived growth factor (PDGF), and Interleukin 4 (IL-4). These molecules initiate signal transduction pathways such as the AKT/mTOR and SMAD pathways that ultimately lead to the proliferation and activation of fibroblasts, which deposit extracellular matrix into the surrounding connective tissue. This process of tissue repair can be a complex one, with tight regulation of ECM synthesis and degradation ensuring maintenance of normal tissue architecture. However, the entire process, although necessary, can lead to a progressive irreversible fibrotic response if tissue injury is severe or repetitive, or if the wound healing response itself becomes deregulated. Fibrosis can occur in many tissues within the body, typically as a result of inflammation or damage, and examples include, but are not limited to, pulmonary fibrosis, cystic fibrosis, idiopathic pulmonary fibrosis, cirrhosis, atrial fibrosis, endomyocardial fibrosis, myocardial infarction, and arterial stiffness.

In one aspect, methods for treating a valvular heart disease in a subject are provided. Methods for treating a valvular heart disease comprise administering to the subject a therapeutically effective amount of at least one therapeutic agent that inhibits hedgehog pathway signalling (i.e., a hedgehog pathway inhibitor).

In another aspect, methods for treating fibrosis in a subject are provided. Methods for treating fibrosis comprise administering to the subject a therapeutically effective amount of at least one therapeutic agent that inhibits hedgehog pathway signalling (i.e., a hedgehog pathway inhibitor).

Hedgehog (Hh) was first described as a genetic mutation that had "spiked" phenotype in the cuticles of Drosophila in the late 1970s. Hh signaling has been implicated in regulation of differentiation, proliferation, tissue polarity, stem cell population and carcinogenesis. Hedgehog signaling molecules in mammals include three Hh homologue ligands (i.e., Sonic hedgehog (Shh), Indian hedgehog (Ihh), and Desert hedgehog (Dhh)), two receptors (i.e., PTCH1 and PTCH2), the key signal transducer smoothened (SMO), and three transcription factors (i.e., GLI1, GLI2, and GLI3). In the absence of Hh ligands, SMO function is inhibited by the transmembrane protein Patched (i.e., PTCH1 and/or PTCH2). Binding of an active Hh ligand to PTCH relieves SMO inhibition, leading to activation of the GLI transcription factors (e.g., GLI1, GLI2, and GLI3). Activated GLI accumulates in the nucleus, where it controls the transcription of hedgehog target genes, which include GLI1. See, e.g., Jia Y et al., *The Hedgehog pathway: role in cell differentiation, polarity and proliferation*, ARCH TOXICOL. (2015) 89(2):179-91. To date, studies have been focused on the role of hedgehog signaling in cancer development and/or metastasis.

To understand the molecular alterations in aortic valves from patients with severe aortic valve stenosis (AS), 16 aortic valve specimens (11 from severe AS patients and 5 from normal aortic valves donated through the autopsy service) were collected. Previous studies have reported elevated activation of several developmental signaling pathways in renal fibrosis, including wnt, hedgehog, notch and TGFbeta signaling. See, e.g., Edeling M, et al. *Developmental signalling pathways in renal fibrosis: the roles of Notch, Wnt and Hedgehog*. NAT REV NEPHROL. 2016; 12(7):426-439. Target genes of these developmental pathways in aortic valves with or without fibrosis were assessed.

FIG. 1 depicts the results of real-time PCR analysis of GLI1 or SPP1 gene expression in aortic valves with or without fibrosis. Healthy aortic valves donated through autopsy services or obtained from patients with aortic valve stenosis were used to extract total RNA for gene expression analysis. Samples #1-11 were from patients with fibrotic aortic valves. Samples #12 and 13 were normal. As indicated by FIG. 1, GLI1 was highly expressed in 7 of 11 fibrotic aortic valves but not in the normal aortic valves. Supporting this observation, hedgehog target gene SPP1 was also highly expressed in all fibrotic tissues. A high level of TGFbeta target gene PAD in all fibrotic tissues were also detected. In contrast to hedgehog and TGFbeta signaling, no significant changes were observed in wnt, notch and hippo/YAP signaling in the fibrotic aortic valves when compared to that of the normal valves. These data indicate that activation of hedgehog and TGFbeta signaling is common in fibrotic aortic valves from AS patients. Although the activation of TGFbeta signaling is well-documented in fibrosis of various tissues, the elevated hedgehog signaling in fibrotic aortic valves was surprising and unexpected.

Figure 2:
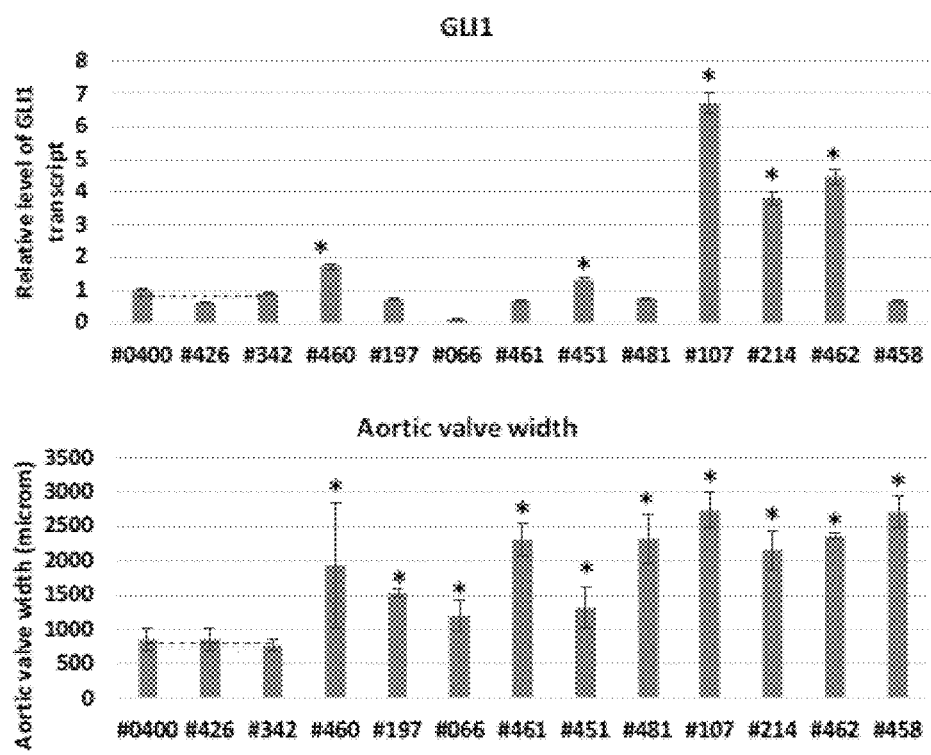
FIG. 2: Bar graphs summarizing results of real-time PCR analysis of GLI1 gene expression in human aortic valves with or without fibrosis (top panel), or aortic valve width measurements from aortic valves with or without fibrosis (bottom panel).

FIG. 2 depicts the results from a second human study in which the aortic valve width and aortic GLI1 expression was determined in three normal aortic valves (specimens #0400, #426, and #342) and 10 fibrotic aortic valves (remaining specimens). As indicated by FIG. 2, significantly elevated expression of hedgehog signalling target gene GLI1 was identified in 5 of 10 human specimens with aortic valve fibrosis, but in none of the aortic valve specimens without fibrosis ($p<0.05$). All specimens with aortic valve fibrosis had a significantly higher measured aortic valve width ($p<0.05$).

Figure 3A:
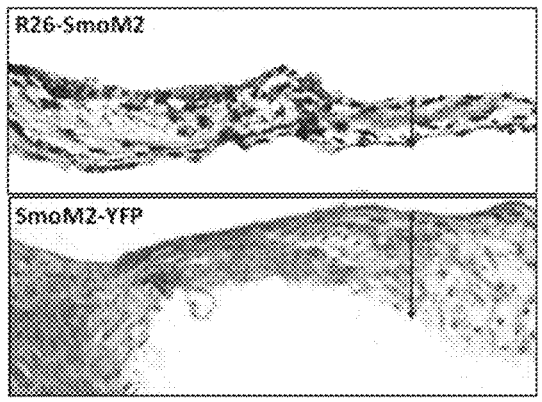
FIG. 3A: Micrograph depicting fibrosis in SmoM2-expressing mice.
Figure 3B:
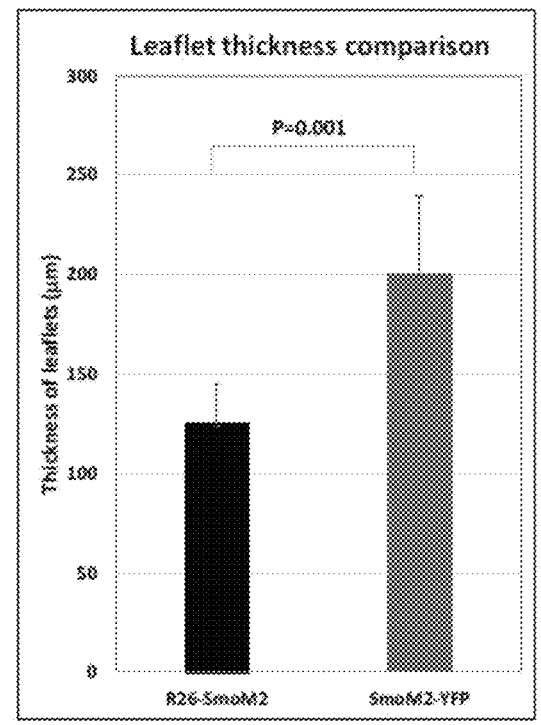
FIG. 3B: Bar graph representing leaflet thickness comparison between SmoM2-expressing mice (SmoM2-YFP) and mice not expressing SmoM2 (R26-SmoM2).
Figure 3C:
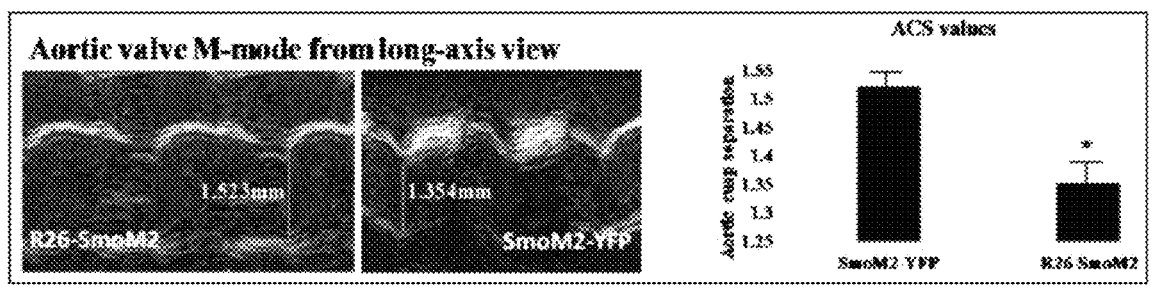
FIG. 3C: Photographs (left two panels) and bar graph (right panel) illustrating results from echocardiogram analysis in aortic valve M-mode from SmoM2-YFP mice and control R26-SmoM2 mice
Figure 4:
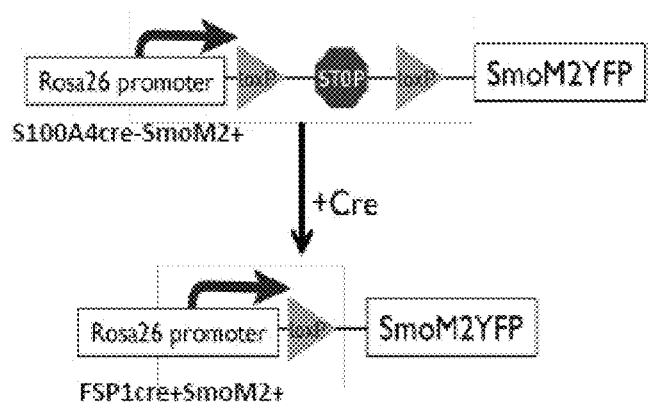
FIG. 4: Schematic illustration of conditional SmoM2 mouse model design.

Hedgehog signalling is sufficient to drive fibrosis in murine aortic valves. This was demonstrated using a mouse model in which an activated form of smoothened—SmoM2—was under the conditional control of an S100A4cre promoter (i.e., FSP1cre). See FIG. 4 for conditional SmoM2YFP mouse model design, which utilizes the Rosa26 promoter and an S100A4cre promoter. See e.g., Xie J, Murone M, Luoh S M, et al. Activating Smoothened mutations in sporadic basal-cell carcinoma. NATURE. 1998; 391(6662):90-92. The resulting SmoM2YFP mice were assessed for aortic valve abnormalities after tissue processing and trichrome staining. Referring now to FIG. 3A, significant fibrosis in SmoM2YFP mice was observed. Measurement of the average leaflet thickness demonstrated that the leaflets from SmoM2YFP mice were thicker (~200 µm) than those from the control R26-SmoM2 mice (~128 µm) ($p=0.001$) (FIG. 3B). It was also tested whether the altered leaflet thickness affected blood flow, as observed in AS patients. Echocardiographic analyses in aortic valve M-mode indicated that mice with fibrotic valves were not well-separated, as were those with the normal valves, as indicated by the aortic cusp separation values (1.35 mm for the fibrotic valves and 1.52 mm for the normal valves; $p=0.001$) (FIG. 3C). These data indicate stenosis in SmoM2YFP mice with fibrotic aortic valves.

Figure 5A:
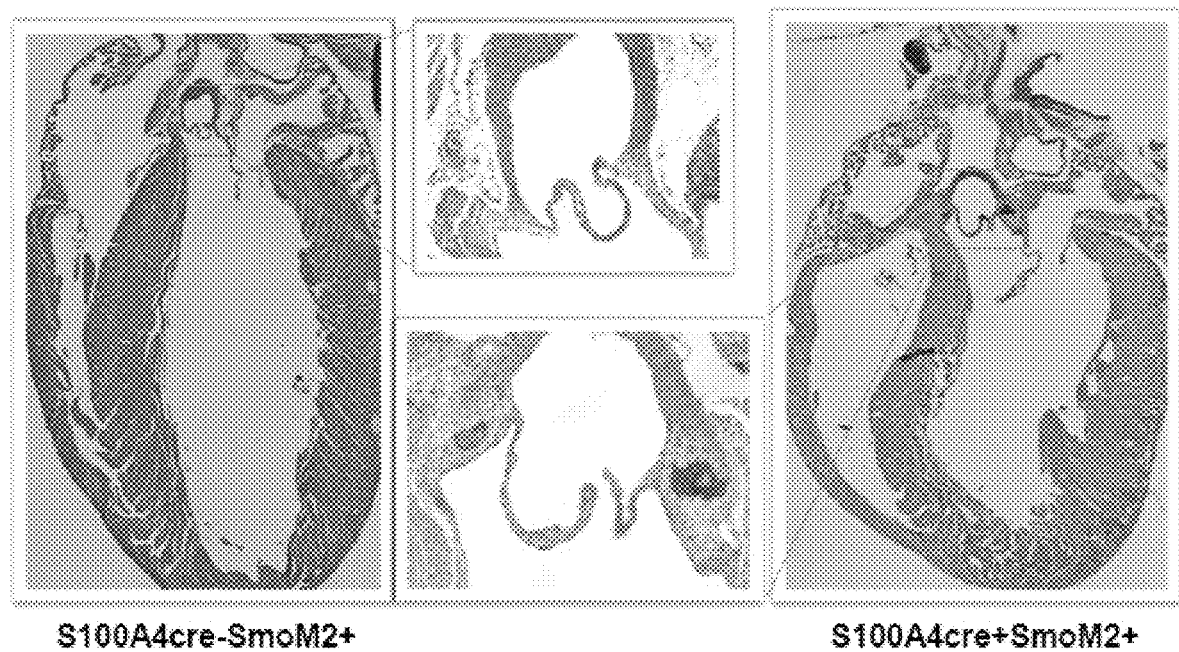
FIG. 5A: Micrograph depicting heart sections and close-up views of aortic valves stained with hematoxylin and eosin from normal mice (S100A4cre−/SmoM2YFP+) and fibrotic mice (S100A4cre+/SmoM2YFP+).
Figure 5B:
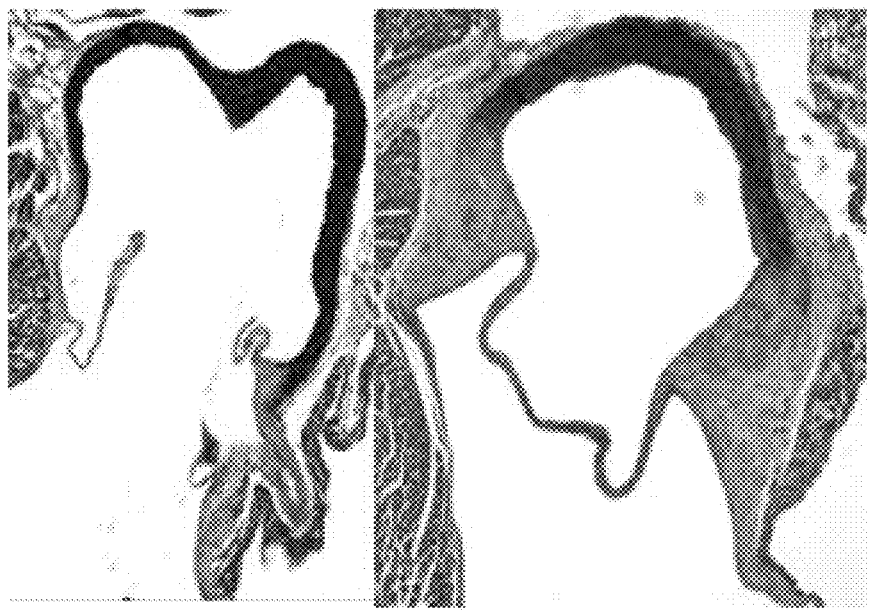
FIG. 5B: Micrograph depicting aortic valves with pentachrome staining from normal mice (S100A4cre−/SmoM2YFP+) and fibrotic mice (S100A4cre+/SmoM2YFP+).
Figure 5C:
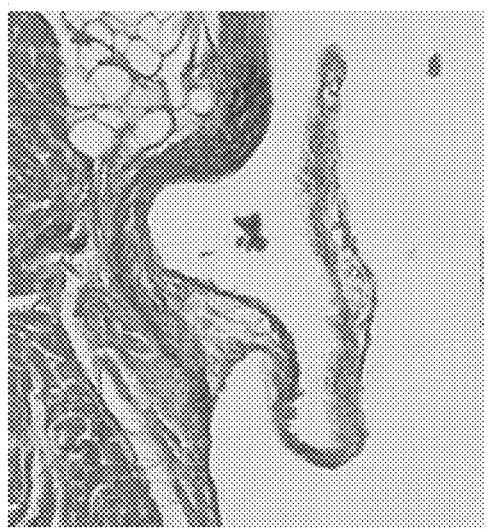
FIG. 5C: Micrograph depicting aortic valves with Sirius Red/Fast Green staining from normal mice (S100A4cre−/SmoM2YFP+) and fibrotic mice (S100A4cre+/SmoM2YFP+).
Figure 5C:
Figure 5D:
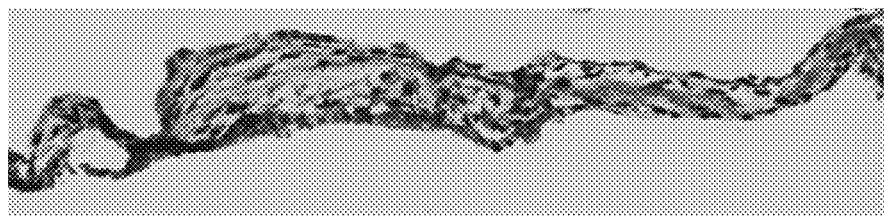
FIG. 5D: Micrograph depicting aortic valves with trichrome staining from normal mice (S100A4cre−/SmoM2YFP+) and fibrotic mice (S100A4cre+/SmoM2YFP+).
Figure 5D:
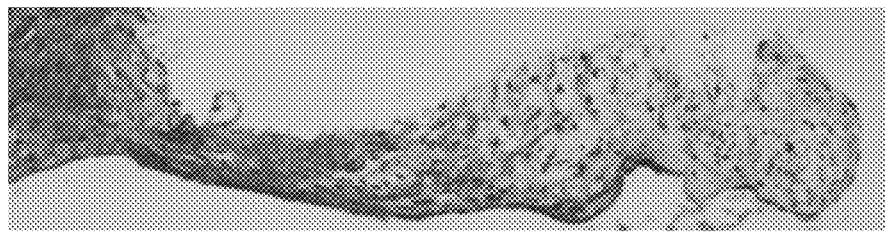

FIGS. 5A-5D depict micrographs of aortic valves of normal mice (S100A4cre−/SmoM2YFP+) and fibrotic mice (S100A4cre+/SmoM2YFP+) with hematoxylin and eosin staining (H&E; FIG. 5A), pentachrome staining (FIG. 5B), Sirius Red/Fast Green staining (FIG. 5C), and trichrome staining (FIG. 5D). As evidenced by the micrographs of FIGS. 5A-5D, histological analysis demonstrates that the activation of hedgehog signaling via expression of SmoM2 results in fibrosis in aortic valves and in aortic roots, phenotypes frequently seen in humans with aortic valve stenosis.

Figure 6:
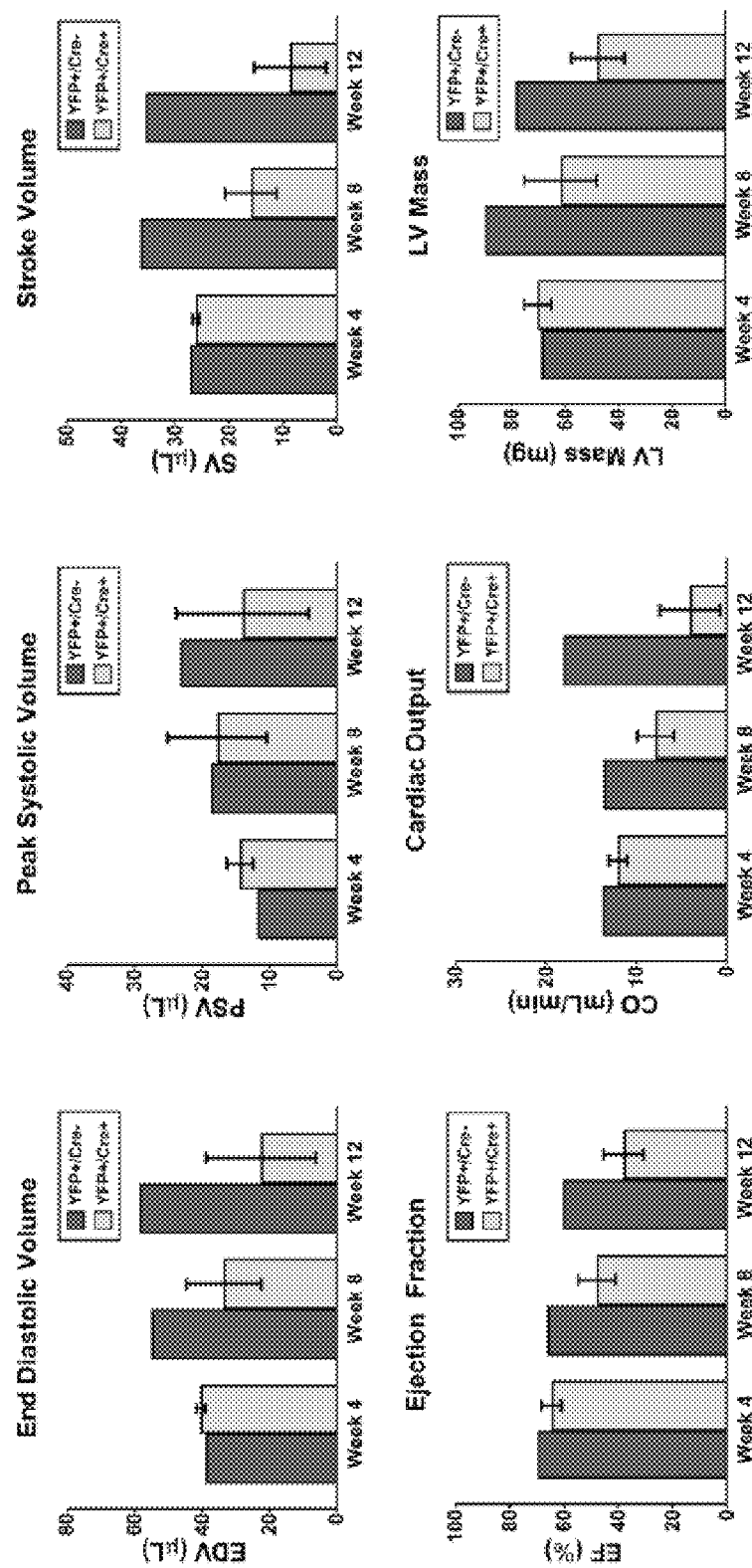
FIG. 6: Bar graphs illustrating results from echocardiography studies conducted with normal mice (S100A4cre−/SmoM2YFP+) and fibrotic mice (S100A4cre+/SmoM2YFP+).
Figure 7:
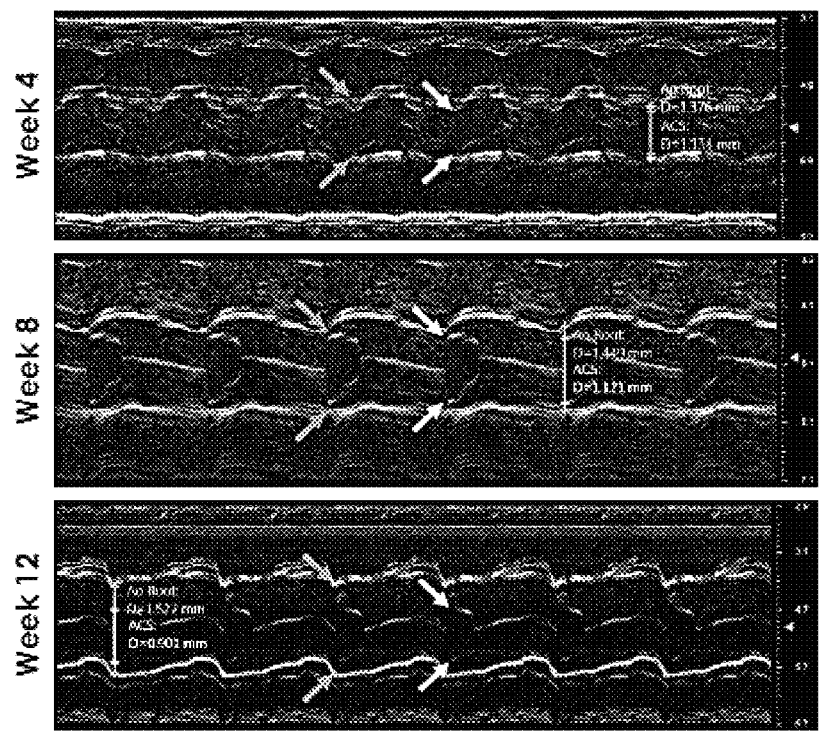
FIG. 7: Representative data depicting reduced aortic cusp separation in a fibrotic mouse (S100A4cre+/SmoM2YFP+).
Figure 8:
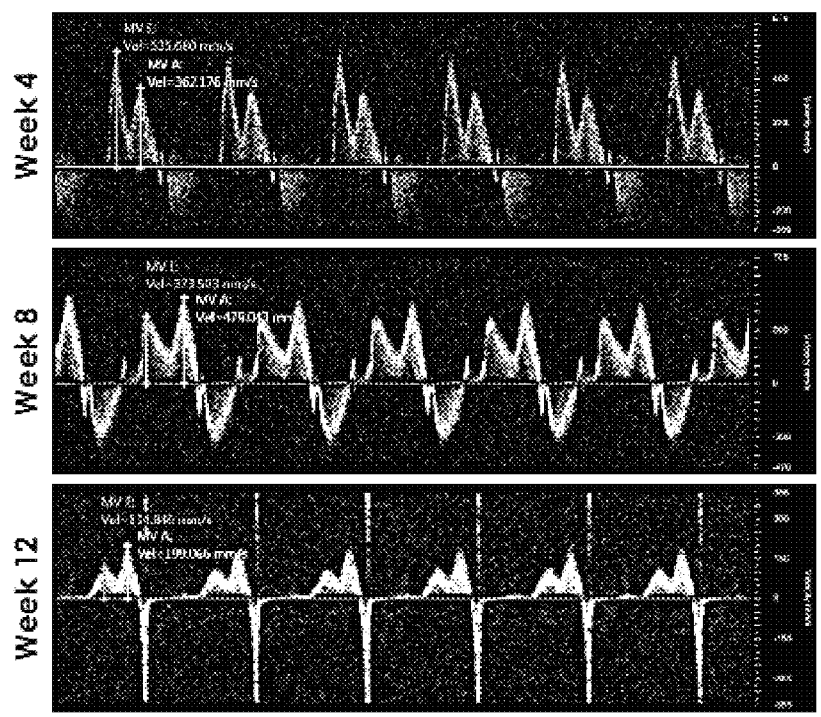
FIG. 8: Representative data depicting reduced cardiac blood flow in a fibrotic mouse (S100A4cre+/SmoM2YFP+).
Figure 9:
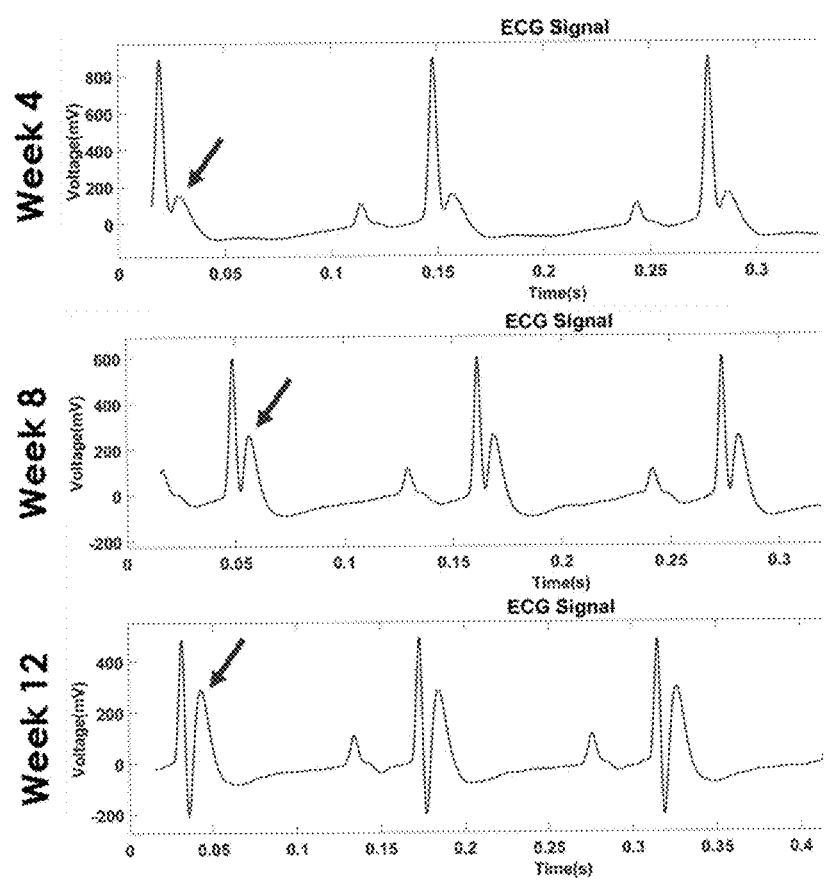
FIG. 9: Representative electrocardiogram (ECG) depicting an elevation in the ST segment in a fibrotic mouse (S100A4cre+/SmoM2YFP+).

Cardiac function analysis revealed SmoM2-expressing mice exhibit progressive cardiac function abnormalities, including reduced left ventricular function (FIG. 6), reduced aortic cusp separation (FIG. 7), reduced cardiac blood flow (FIG. 8), and an elevation in the ST segment in ECG (FIG. 9).

Together, the data from the human aortic valve specimens and the two mouse models demonstrate an important role for hedgehog signaling in aortic valve fibrosis and in aortic valve stenosis, identifying hedgehog signaling as a target for treatment of valvular heart diseases such as aortic valve stenosis.

In some embodiments, treating a valvular heart disease in a subject comprises administering to the subject a therapeutically effective amount of at least one therapeutic agent that inhibits hedgehog pathway signaling by inhibiting smoothened (SMO) (i.e., an SMO antagonist); inhibiting GLI1, GLI2, and/or GLI3 (i.e., an antagonist of GLI1, GLI2, and/or GLI3); inhibitors of hedgehog ligands (i.e., Hh antagonists); activating and/or enhancing inhibitory activity of PTCH1 and/or PTCH2 (i.e., agonists of PTCH1 and/or PTCH2), or any combination thereof.

In certain embodiments, hedgehog pathway inhibitors include, but are not limited to, vismodegib, sonidegib, BMS-833923, TAK-441, glasdegib, taladegib, saridegib, arsenic trioxide, PF-5274857, MRT-92, CUR61414, GANT-58, GANT-61, RU-SKI 43, Shh monoclonal antibody 5E1, itraconazole, and robotnikinin. Other hedgehog pathway inhibitors known in the art, as well as newly discovered inhibitors, are similarly contemplated by the present disclosure. Hedgehog pathway inhibitors approved by the U.S. Food and Drug Administration for use in humans include the SMO antagonists vismodegib, sonidegib, and glasdegib, and the GLI1 and GLI2 inhibitor arsenic trioxide. Other SMO antagonists include BMS-833923, taladegib, saridegib, PF-5274857, TAK-441, MRT-92, and CUR61414, many of which are or have undergone clinical trials. Other GLI inhibitors include GLI antagonists (GANTs) GANT-58 and GANT-61. Hedgehog ligand inhibitors include indirect SHH inhibitor RU-SKI 43, and SHH monoclonal antibody 5E1.

In some embodiments, the methods for treating the valvular heart disease also include identifying a subject at risk of having a valvular heart disease, identifying a subject having a valvular heart disease, and/or identifying a subject having a symptom related to a valvular heart disease. In certain embodiments, the subject has been diagnosed with a valvular heart disease and/or a related symptom. Diagnostic methods for valvular heart disease include, but are not limited to, echocardiography, electrocardiogram, chest x-ray, cardiac catheterization, stress test, and cardiac MRI.

In certain embodiments, the therapeutically effective amount of the at least one hedgehog pathway inhibitor is administered daily to the subject in a single dose. In other embodiments, the hedgehog pathway inhibitor is administered daily to the subject in multiple doses. In some embodiments, a single dose (i.e., each dose of the at least one hedgehog pathway inhibitor) or single dosage form contains from about 15 mg to about 1000 mg, from about 50 mg to about 500 mg, from about 50 mg to about 400 mg, from about 50 mg to about 300 mg, from about 50 mg to about 250 mg, from about 100 mg to about 200 mg, about 25 mg, about 50 mg, about 100 mg, about 150 mg, about 200 mg, or about 250 mg of the at least one hedgehog pathway inhibitor.

In certain embodiments, commercially available hedgehog inhibitors are used in accordance with methods described herein in their commercially available dosage forms. For example, vismodegib is available as 150 mg capsules, sonidegib is available as 200 mg capsules, glasdegib is available as 25 mg and 100 mg tablets, and arsenic trioxide is available as an injectable solution (1 mg/ml). In some embodiments, dosing of the commercially available hedgehog pathway inhibitor for use in accordance with the methods described herein is the same as that prescribed for the inhibitor's currently approved use. For example, in some embodiments, vismodegib is administered to a subject having a valvular heart disease in a single daily dose of 150 mg.

Certain commercially available hedgehog pathway inhibitors result in intolerable adverse reactions in some patients. Adverse reactions may include muscle spasms, weight loss, fatigue, and decreased appetite. Strategies have been devised to overcome such adverse reactions while maintaining treatment. For example, dosing may be interrupted for up to four weeks. Similar strategies can be employed when commercially available hedgehog pathway inhibitors are used in accordance with the present methods.

In other embodiments, commercially available hedgehog inhibitors are used in accordance with the present methods in a dosage form other than its commercially available dosage form. Dosing with such a new dosage form is carried out in accordance with the present disclosure.

In some embodiments, the valvular heart disease comprises at least one disease process involving one or more of the four valves of the heart. In certain embodiments, the valvular heart disease treatable by the methods disclosed and described herein is one or more of: stenosis, including aortic valve stenosis, mitral valve stenosis, tricuspid valve stenosis, and pulmonary valve stenosis; regurgitation, including aortic valve regurgitation, mitral valve regurgitation, tricuspid valve regurgitation, and pulmonary valve regurgitation; calcification, including aortic valve calcification, mitral valve calcification, tricuspid valve calcification, and pulmonary valve calcification; and heart murmur associated with dysfunctional valves.

In other embodiments, the fibrosis treatable by the methods disclosed and described herein is one or more of pulmonary fibrosis, cystic fibrosis, idiopathic pulmonary fibrosis, cirrhosis, atrial fibrosis, endomyocardial fibrosis, myocardial infarction, and arterial stiffness.

EXAMPLES

Experimental Procedures

Human specimens. Human aortic valve specimens with fibrosis (n=11) were collected as discarded human materials following ACR and pathological diagnosis. Normal aortic valves, n=4) were donated through the autopsy services, and use of all human specimens was approved by institutional research board.

RNA extraction, RT-PCR, and analysis. Total RNAs were extracted from tissues using TRI-RNA reagent (Sigma). 1 µg of total RNA was reverse-transcribed into cDNA. Real-time quantitative PCR analyses were performed using Taqman primers and probes. Triplicate CT values were analyzed in using the comparative CT($\Delta\Delta$CT) method. The amount of target ($2^{-\Delta\Delta CT}$) was obtained by normalization to an endogenous reference (Gapdh for mice and GAPDH for humans) and relative to a calibrator. See, e.g., Fan Q. et al., *Defective TGF-β signaling in bone marrow-derived cells prevents hedgehog-induced skin tumors*, CANCER RES. (2014) 15; 74(2):471-483.

Fibroblast-specific expression of SmoM2 in mice and functional analyses. FSP1-cre mice were mated with R26-SmoM2 mice to generate FSP1-Cre$^+$/R26-SmoM2$^+$ mice. Tissues with aortic valves from mice were processed to detect tissue fibrosis by Trichrome staining (with blue staining as fibrotic site). Echocardiography was performed with Visual Sonics Vevo 2100 high-resolution ultrasound system.

Transgenic mice. Research with mice was approved by institutional IACUC approval. FSP1-cre mice were crossed with Rosa26-SmoM2-YFP mice to generate mice with cre recombinase expression and expression of SmoM2. When mice appear sick (~7-8 weeks), ultrasound analysis of aortic valves for any dysfunction were performed. The heart tissues were processed to obtain H&E and trichrome staining.

Ultrasound detection of dysfunctional aortic valves. Mice were subjected to echocardiography using Vevo 2100 high frequency ultrasound system. Aortic valve leaflets were visualized across the cardiac cycle at 1000 frames/second. The Aortic Cusp Separation (ACS) was calculated from the M-mode echocardiography. See, e.g., Chu Y et al. *Fibrotic Aortic Valve Stenosis in Hypercholesterolemic/Hypertensive Mice*. ARTERIOSCLER THROMB VASC BIOL. 2016; 36(3):466-474.

Histology and special staining. Heart tissues were fixed in 4% paraformaldehyde overnight before being processed for paraffin embedding. Tissues were sectioned at 5 mm, and processed with Sirius Red/Fast Green, Masson's Trichrome, or Movat Pentachrome staining.

Statistical analysis. All experiments have at least 3 biological repeats. In real time PCR analysis, standard deviation values (shown I error bars) were used to indicate reproducibility of the experiments. For mouse studies, at least 5 mice in each group were assessed, with abnormal aortic valves in all SmoM2 expressing mice and none in the wild type mice (no SmoM2 expression). Student t test was used to detect differences between two samples, with p value<0.05 as statistically significant.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

I claim:

1. A method of treating aortic valve stenosis in a subject, the method comprising:
administering to the subject a therapeutically effective amount of at least one hedgehog pathway inhibitor, wherein the at least one hedgehog pathway inhibitor comprises at least one of: vismodegib, sonidegib, BMS-833923, TAK-441, glasdegib, taladegib, saridegib, arsenic trioxide, PF-5274857, MRT-92, GANT-58, GANT-61, RU-SKI 43, sonic hedgehog (Shh) monoclonal antibody 5E1, itraconazole, and robotnikinin.

2. The method according to claim 1, wherein the at least one hedgehog pathway inhibitor is selected from: at least one smoothened (SMO) antagonist; at least one antagonist of GLI1, GLI2, and/or GLI3; or any combination thereof.

3. The method according to claim 1, further including the step of:
identifying a subject at risk of having aortic valve stenosis and/or identifying a subject having aortic valve stenosis or a symptom related to the aortic valve stenosis.

4. The method according to claim 1, wherein the aortic valve stenosis comprises at least one disease process involving one or more of the four valves of the heart.

5. The method according to claim 1, wherein the therapeutically effective amount of the at least one hedgehog pathway inhibitor is administered daily to the subject in a single dose.

6. The method according to claim 1, wherein the therapeutically effective amount of the at least one hedgehog pathway inhibitor is administered daily to the subject in multiple doses.

7. The method according to claim 1, wherein the therapeutically effective amount of the at least one hedgehog pathway inhibitor is administered to the subject in doses from about 15 mg to about 1000 mg, from about 50 mg to about 500 mg, from about 50 mg to about 400 mg, from about 50 mg to about 300 mg, from about 50 mg to about 250 mg, from about 100 mg to about 200 mg, about 50 mg, about 100 mg, about 150 mg, about 200 mg, or about 250 mg of the hedgehog pathway inhibitor.

8. The method according to claim 1, wherein the at least one hedgehog pathway inhibitor is vismodegib and/or sonidegib.

9. The method according to claim 1, wherein the subject comprises a human or an animal.

10. The method according to claim 1, wherein the subject is diagnosed with aortic valve stenosis and/or a related symptom.

* * * * *